United States Patent [19]

Sell

[11] Patent Number: 4,652,120
[45] Date of Patent: Mar. 24, 1987

[54] PHOTOTHERMAL METHOD OF MEASURING FLUID VELOCITY

[75] Inventor: Jeffrey A. Sell, Huntington Woods, Mich.

[73] Assignee: General Motors Corporation, Detroit, Mich.

[21] Appl. No.: 648,815

[22] Filed: Sep. 10, 1984

[51] Int. Cl.⁴ .................... G01P 3/36; G01N 21/41
[52] U.S. Cl. .................................. 356/28; 356/129; 356/432; 356/436
[58] Field of Search ............... 356/28, 28.5, 129, 318, 356/432, 436, 437, 438

[56] References Cited

U.S. PATENT DOCUMENTS 3,807,228  4/1974  Matzuk .............................. 73/194 E
3,950,104  4/1976  Munk ................................. 356/128

OTHER PUBLICATIONS

W. Herrman et al, IBM Tech. Discl. Bul., vol. 21, #10, Mar. 1979.
W. Herrman et al, Infrared Physics, Aug. 1979, p. 455.
W. B. Jackson et al, Applied Optics, vol. 20, #8, Apr. 15, 1981.

Primary Examiner—Stephen C. Buczinski
Attorney, Agent, or Firm—Warren D. Hill

[57] ABSTRACT

A method of measuring the velocity of a fluid by nonintrusive means comprises passing a pulsed pump laser beam through the fluid wherein the fluid contains a constituent absorbing the wavelength of the laser so that a temperature gradient, and therefore an index of refraction gradient, occurs in the laser beam path; and a probe laser beam is passed transversely to the pump laser beam and is deflected by the heated portion of the fluid by an amount which is proportional to the concentration of the absorbing constituent and inversely proportional to the velocity of the fluid; measuring the beam deflection and calculating from that the fluid velocity, if the concentration of the absorbing constituent is known, or calculating the relative velocity if the concentration of the absorbing constituent is constant. The apparatus is similar to that used for photothermal deflection spectroscopy and involves a pair of crossed laser beams, one for pumping the medium and one for probing the medium, a probe beam deflection sensor, and electronic circuitry for analyzing the measured deflection signal.

4 Claims, 4 Drawing Figures

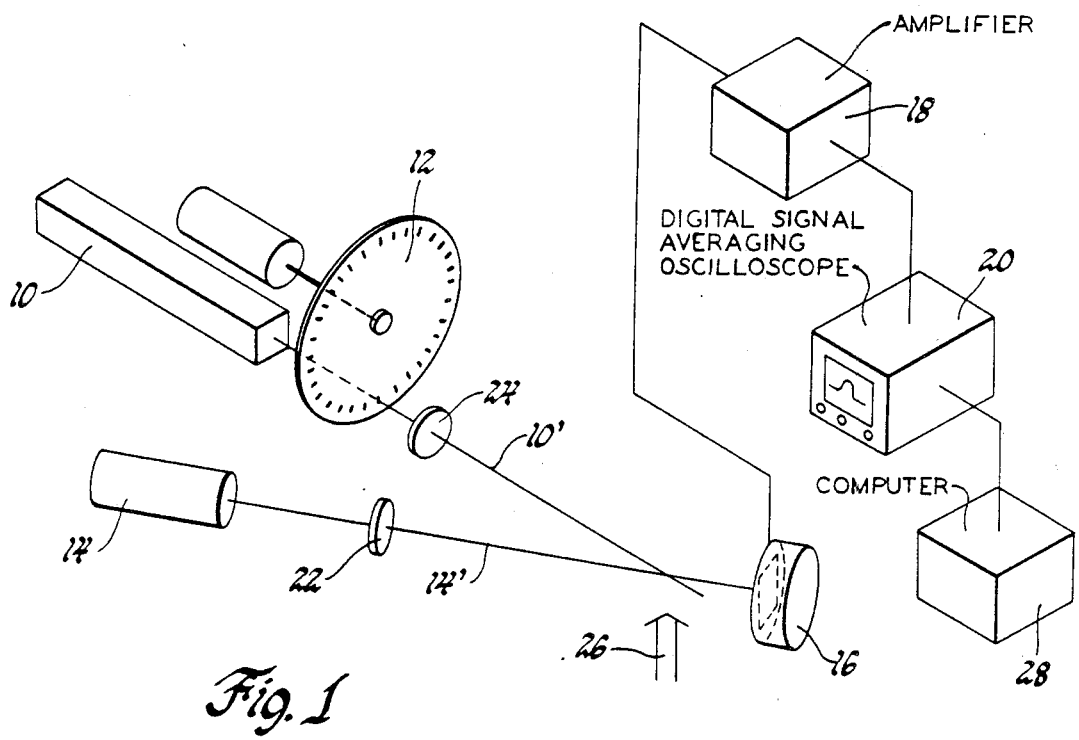
*Fig. 1*
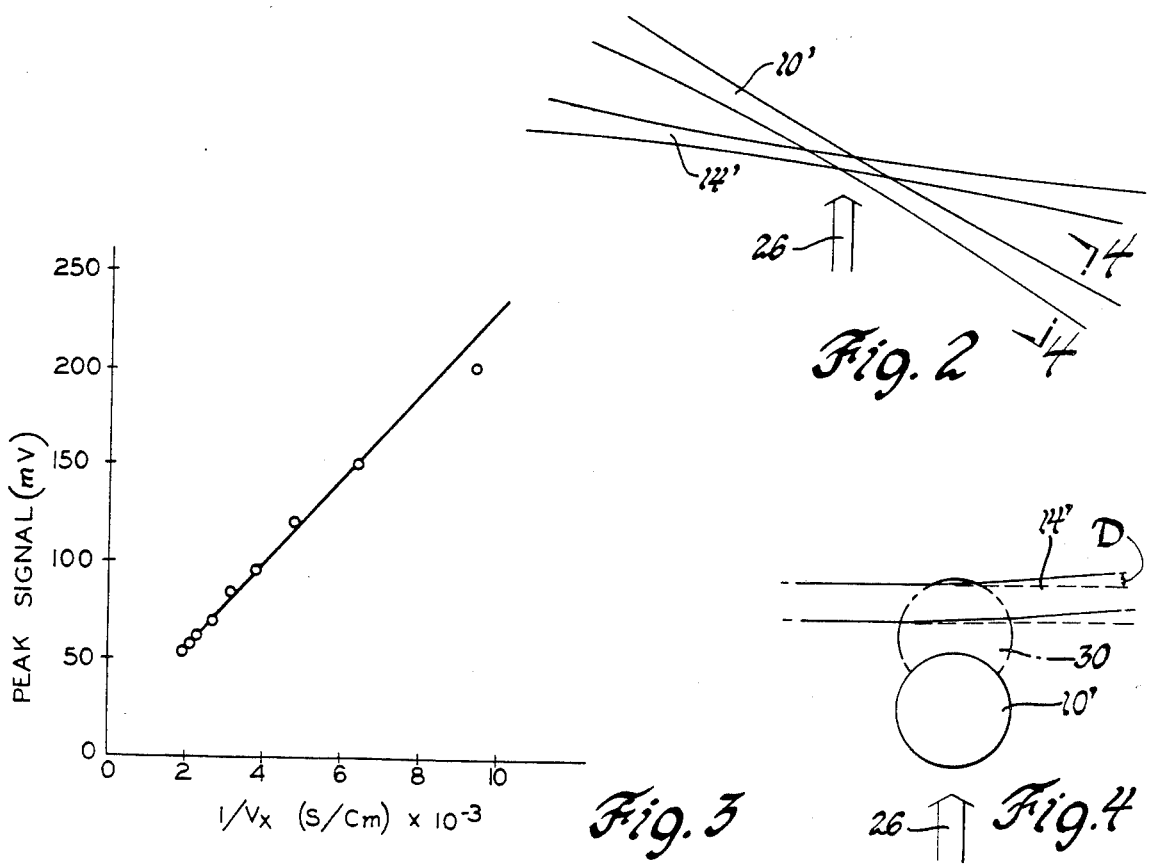
*Fig. 2*
*Fig. 3*
*Fig. 4*

PHOTOTHERMAL METHOD OF MEASURING FLUID VELOCITY

This invention relates to an optical method of measuring fluid velocity and especially to a nonintrusive photothermal method of measuring the local velocity in a very small volume of a fluid.

In making studies of physical and chemical phenomena in fluids, such as the combustion of gases or turbulence in liquids or gases, it is desired to measure the fluid velocity at particular points in the fluid, independently of dynamic conditions in other portions of the fluid and without intrusion of a mechanical probe. By measuring many local velocities in a fluid, turbulence, stream velocity, and other dynamic fluid conditions can be mapped. Similarly, by measuring the local velocity of gases undergoing combustion or other chemical reaction, the effects of the reaction on velocity (or vice versa) can be investigated.

Photothermal deflection spectroscopy (PDS) is a well known optical measurement technique involving two crossed laser beams for use in stagnant gases or in liquids and/or solids where thermal conduction dominates the heat transfer. This technique is capable of measuring either very small absorption coefficients or low sample concentrations and has been used, for example, to examine the spectra of solid surfaces and absorption in thin films and liquids. My investigation of PDS revealed that it can be used in a flowing stream of gas where forced convection dominates the heat transfer, and I have discovered the quantitative effects of velocity on the PDS measurements.

It is therefore a general object of this invention to provide a method of measuring local velocities in a fluid and particularly to such a method which is both nonintrusive and independent of fluid velocity in surrounding portions of the fluid. It is a further object of the invention to provide such fluid velocity measurement by photothermal deflection techniques.

The method of the invention is carried out by passing a pulsed pump laser beam through a fluid containing a constituent which absorbs energy from the laser beam to heat a portion of the fluid and establish a temperature gradient which results in a gradient in the index of refraction; passing a probe laser beam transversely through the heated portion of the fluid such that the probe beam is deflected by reason of the gradient in the index of refraction; measuring the peak deflection of the probe beam; and calculating the local velocity of the heated portion from the measured deflection.

The above and other advantages of the invention will become apparent from the following description and accompanying drawings, wherein:

FIG. 1 is a schematic view of photothermal deflection apparatus for carrying out the method of the invention;

FIG. 2 is an enlarged view of the laser beam interaction region of the apparatus of FIG. 1;

FIG. 3 is a graph of the relationship between the measured deflection signal and the velocity in the region being studied, and FIG. 4 is a view taken along line 4—4 of FIG. 2 illustrating the beam deflection.

A diagram of the apparatus is shown in FIG. 1. The pump laser 10 shown is a Model 570 $CO_2$ laser manufactured by Apollo Lasers of Los Angeles, Calif., which is capable of producing more than 50 watts CW power on each of approximately 25 different $CO_2$ lasing transitions. The P(14) line of the $CO_2$ 10.6 micron band is selected by a grating in the laser. For this method, the laser can be operated CW, Q-switched, or electrically modulated. When in the CW operational mode, a mechanical chopper 12 is employed which has a duty cycle of 3.3% and is operated at a speed which gives pulses at 100 Hz. In the electrically chopped mode, the current applied to the laser 10 is on for 0.2 ms and repeats at 100 Hz to provide a duty cycle of 2%. This latter mode is the simplest one—not requiring the mechanical chopper 12. However, the actual laser output is not temporally rectangular, having a tail that lasts at least 0.2 ms beyond the time when the current is turned off, but this tail does not interfere with measuring the peak signal as required for this method. In the Q-switched mode, the $CO_2$ laser pulse is very short (about 1 microsecond) and has high peak power (about 100 kwatt).

A probe laser 14 is a Model 145-01 He-Ne laser manufactured by Spectra-Physics, Inc., of San Jose, Calif. The power, which is relatively unimportant for this purpose, is about 1 mW.

A lateral cell detector 16 (Model 386-22-21-251 manufactured by Silicon Detector Corporation of Newbury Park, Calif.) is employed for measuring the deflection of the probe laser beam. It is capable of measuring shifts in the position of the laser beam of the order of $\pm 10^{-4}$ cm. Operational amplifiers in amplifier 18 amplify the signal; the bandwidth of this circuit is greater than 1 MHz.

For data collection, a Model 468 digital signal averaging oscilloscope 20 manufactured by Tektronix, Inc., of Beaverton, Oreg., is used to store the data as well as to display the deflection curves. The signal averaging feature of this oscilloscope is especially useful for improving the signal/noise ratio. All results discussed herein were obtained by averaging 256 laser pulses. Other data acquisition devices could be employed, e.g., a computer with an A/D converter, a transient digitizer, or a boxcar averager. A computer 28 coupled to the oscilloscope 20 analyzes the collected data to calculate velocity.

The optics in this apparatus are quite simple. A $BaF_2$ lens 22 of 15.2 cm focal length is used to focus the He-Ne probe laser beam 14' to a Gaussian spot of 1/e intensity radius of 79 microns. The $CO_2$ pump laser beam 10' is focused with a ZnSe lens 24 of 16.5 cm focal length to an average radius of about 150 microns, although the intensity profile is not Gaussian. The pump laser beam 10' is moved relative to the probe laser beam 14' by moving the lens 24 that focuses the $CO_2$ beam. This equipment is easy to align optically since there are no phase-matching conditions and the angle between the two lasers is somewhat arbitrary.

As shown in FIGS. 2 and 4, arrow 26 indicates the direction of flow of gas or other fluid to be measured. The beams 10' and 14' may overlap where they cross, or there may be a small spatial displacement in the direction of fluid flow. In FIG. 4 the pump beam 10' is shown in cross section and the heated portion 30 of the gas is shown in a location downstream of the beam 10' as it would be a short time after the pump beam pulse. The heated portion 30 acts as a cylindrical lens deflecting the probe beam 14' through an angle D from a straight path which is shown in dotted lines. The maximum deflection signal is obtained where the probe beam axis is downstream of the pump beam axis by, say, 200 microns, so that the probe beam passes through flowing fluid which has had maximum exposure to the pump laser beam—and therefore experiences maximum heating. The displacement of the two laser beams for maximum signal depends on the fluid velocity, but the determination of the fluid velocity does not require that the beams be positioned for maximum signal. The two beams cross at an angle of 20° which determines the interaction length (about 0.1 cm) of the lasers. The interaction volume occupied by the crossed, spaced laser beams is about $1.5 \times 10^{-4}$ cm$^3$; this volume defines the spatial resolution.

In order for the fluid to be heated by the pump beam 10', the fluid must contain a constituent which absorbs the wavelength of the pump beam. Accordingly, for investigation of a particular fluid, it is necessary to select a pump laser which provides a suitable wavelength. Alternatively, the fluid may be seeded upstream with a constituent which absorbs the pump beam wavelength. For example, to obtain the data in FIG. 3, a small amount of ethylene was added to nitrogen to obtain a measurement of the nitrogen flow. The ethylene does absorb the particular pump beam wavelength described above and the peak detector signal is proportional to the concentration of the ethylene. The dependence of the signal strength on the ethylene concentration was found to be linear over a range of 1 ppm to 10,000 ppm. Thus, in order to obtain any velocity data from the peak deflection signal, the concentration of the ethylene or other absorbing constituent must be held constant or at least be known for each data point. Many absorbing species may be used with the specified pump laser and, of course, other species are appropriate for use with other lasers. The peak magnitude of the beam deflection was measured and was found to be proportional to c/v, where c is the concentration of the absorbing constituent of the fluid, and v is the fluid velocity. By maintaining the concentration c constant, the relative velocity is readily determined. In the case of the mechanically and electrically modulated beams, the product of the laser peak power, the absorption coefficient of the gas, and the concentration of the absorbing gas should be approximately $1.5 \times 10^{31}$ $^2$ cm$^{-1}$ watt to get an easily measurable signal.

The temperature of the fluid must also be constant (within 10° to 20° Celsius) for the present method to be accurate. The pump laser heats the gas only a few degrees (for absorber concentrations below 10,000 ppm and pump laser power below about 1 watt average), so that this condition is not violated by the pump laser.

As shown by the measured data points in FIG. 3, when the ethylene concentration is held to a constant value (in this case, 1,019 ppm) the peak detector signal is inversely proportional to the gas velocity. At low gas velocities, thermal conduction influences the deflection signal so that this velocity measuring method is limited to higher velocities. For the present study in nitrogen, the lower limit is about 100 cm/sec, while the upper limit is about 500 cm/sec, or even higher. The lower limit is determined by the point at which thermal conduction can no longer be ignored in the heat transfer. This depends on the density, heat capacity, and thermal conductivity of the fluid as well as the displacement of the pump and probe beams. The upper limit is determined by the ability of the technique to measure small displacements of the probe beam which depends on the sensitivity of the detector, the noise (primarily that due to turbulence), the absorbing gas absorption coefficient, and the pump laser power.

In summary, the method of the invention comprises passing a pulsed pump beam 10' from the CO$_2$ laser 10 through the fluid being measured to heat the fluid in the path of the beam, and sensing the temperature gradient of the heated fluid by a probe beam 14' from the helium-neon (He-Ne) laser 14, which beam crosses (but not necessarily intersects) the path of the pump beam 10' to intercept the heated portion 30 of the fluid. The temperature gradient of the fluid controls the index of refraction gradient of the fluid so that the heated portion 30 serves as a lens and deflects the probe beam 14' by an amount proportional to c/v. When the concentration of the absorbing constituent is known, the absolute velocity can be calculated—assuming the apparatus has been calibrated by comparison with a standard. Otherwise, the relative velocity is readily measured if the concentration is a constant.

The above analysis assumes that the gas velocity is in a direction perpendicular to the plane of the crossed laser beams (i.e., the x direction), where the plane is considered to be that plane which passes through at least one of the beams and is parallel to the other beam. However, if there is a component of gas velocity parallel to the plane of the laser beams and perpendicular to the probe beam 14' (i.e., the y direction), the probe beam would then have a component of deflection in the plane of the laser beams. The detector 16 has the ability to measure separately the x and y deflections of the probe beam so that it is possible to analyze the two sets of detector outputs to determine the vector resultant of the fluid velocity. When making such a two-dimensional measurement, it is preferred to place the two laser beams in the same plane so that their beam axes do intersect. Then the x and y deflection components will be inversely proportional to the x and y velocity components. The interaction volume will be about $6.4 \times 10^{-5}$ cm$^3$.

The apparatus of FIG. 1 makes it possible to modulate the pump beam to produce a rapid series of short pump pulses so that many measurements at a given sample volume in the fluid stream may be made in a very short time period. The averaging oscilloscope 20 allows averaging of those measurements to effectively filter noise from the data and increase the resolution of the measured value. For many uses, however, the signal-to-noise ratio has been found to be high enough that a single measurement at each data point is sufficient and the averaging technique is not required. In this case, the time resolution of the velocity measurement would be very good.

This photothermal deflection method of measuring fluid velocity has high spatial resolution, it is a nonintrusive optical method applicable over a wide range of velocities, and optical alignment is easily accomplished. Many types of lasers perform effectively as pump lasers provided the wavelength matches the absorption band of the absorbing gas.

The embodiments of the invention for which an exclusive property or privilege is claimed are defined as follows:

1. The method of measuring the local velocity in a fluid by photothermal deflection comprising the steps of:

heating a portion of the fluid by passing a pulsed focused laser pump beam through the fluid, the pump beam having a wavelength which is absorbed by a constituent of the fluid to establish a temperature gradient, whereby the temperature gradient causes a gradient in the index of refraction;

detecting the temperature gradient in a local volume of the fluid by passing a laser probe beam transversely through the heated portion of the fluid to cause deflection of the probe beam, whereby the deflection magnitude is a direct function of the concentration of the absorbing constituent and an inverse function of the local velocity;

measuring the peak deflection of the probe beam; and calculating the local velocity for a given concentration of the absorbing constituent from the measured deflection.

2. The method of measuring the relative local velocity in a fluid by photothermal deflection comprising the steps of:

heating a portion of the fluid by passing a pulsed focused laser pump beam through the fluid, the pump beam having a wavelength which is absorbed by a constituent of the fluid to establish a temperature gradient and a gradient in the index of refraction, the absorbing constituent having a substantially constant concentration;

detecting the temperature gradient in a local volume of the fluid by passing a laser probe beam transversely through the heated portion of the fluid to cause deflection of the probe beam, whereby the deflection magnitude is an inverse linear function of the local velocity;

measuring the peak deflection of the probe beam; and calculating the relative local velocity from the measured deflection.

3. The method of measuring the local velocity in a fluid by photothermal deflection comprising the steps of:

heating a portion of the fluid by passing a pulsed focused laser pump beam through the fluid, the pump beam having a wavelength which is absorbed by a constituent of the fluid to establish a temperature gradient, whereby the temperature gradient causes a gradient in the index of refraction;

passing a laser probe beam through the fluid transverse to and intersecting the pump beam to define a plane, the index of refraction gradient causing a peak beam deflection having a peak magnitude inversely proportional to the local velocity of a volume of fluid at the beam intersection;

measuring the peak deflection of the probe beam in a first direction perpendicular to the plane to obtain data on the local velocity in the first direction;

measuring the peak deflection of the probe beam in a second direction parallel to the plane and perpendicular to the probe beam to obtain data on the local velocity in the second direction; and calculating the local velocity from the deflection data in the first and second directions.

4. The method of measuring the local velocity in a fluid stream by photothermal deflection comprising the steps of:

adding a known concentration of an absorbing constituent to a fluid stream upstream of a measuring site;

heating a portion of the fluid at the measuring site by passing a pulsed focused laser pump beam through the stream, the pump beam having a wavelength which is absorbed by the absorbing constituent to establish a temperature gradient, whereby the temperature gradient causes a gradient in the index of refraction;

detecting the temperature gradient in the fluid by passing a laser probe beam transversely through the heated portion of the fluid to cause deflection of the probe beam, whereby the deflection magnitude is a linear inverse function of the local velocity;

measuring the peak deflection of the probe beam; and calculating the local velocity from the measured deflection.

* * * * *